United States Patent

Yang

[11] Patent Number: 6,083,183
[45] Date of Patent: Jul. 4, 2000

[54] WAISTBAND DEVICE

[76] Inventor: Shyi-Mou Yang, 58, Ma Yuan West St., Taichung, Taiwan

[21] Appl. No.: 09/162,899

[22] Filed: Sep. 29, 1998

[51] Int. Cl.[7] .................................................... A61F 5/00
[52] U.S. Cl. .................................. 602/19; 2/312; 2/318; 2/44; 2/311; 128/876
[58] Field of Search ............................... 2/311, 312, 318, 2/319, 92, 338, 44, 45, 69; 128/874, 875, 876; 450/155, 186; 297/466; 602/19, 32

[56] References Cited

U.S. PATENT DOCUMENTS

| | | | |
|---|---|---|---|
| 1,028,346 | 6/1912 | Franks | 2/94 |
| 4,813,080 | 3/1989 | Toso | 2/94 |
| 5,001,791 | 3/1991 | Toso | 5/432 |
| 5,083,554 | 1/1992 | Toso | 128/78 |
| 5,542,433 | 8/1996 | Saupe | 128/869 |
| 5,643,184 | 7/1997 | Toso | 602/19 |

FOREIGN PATENT DOCUMENTS 503575  3/1976  Russian Federation ..................... 2/94

*Primary Examiner*—Diana Oleksa
*Assistant Examiner*—Katherine Moran

[57] ABSTRACT

A waistband device has a rectangular cushion, a first connecting band disposed on a first lateral of the rectangular cushion, a second connecting band disposed on a second lateral of the rectangular cushion, a first belt connected to the first connecting band, a second belt connected to the second connecting band, a first keeper disposed on the first belt, a first soft pad disposed on the first belt, a male fastener disposed on a distal end of the first belt, a first loop hole defined by the first belt, a second keeper disposed on the second belt, a second soft pad disposed on the second belt, a female fastener disposed on a distal end of the second belt, and a second loop hole defined by the second belt.

2 Claims, 3 Drawing Sheets

WAISTBAND DEVICE

BACKGROUND OF THE INVENTION

The present invention relates to a waistband device. More particularly, the present invention relates to a waistband device which helps to straighten a back of a user.

A back of a user may be bent after a long period of sitting. It is necessary to straighten the back of the user while the back is hunchbacked slightly.

SUMMARY OF THE INVENTION

An object of the present invention is to provide a waistband device which helps to straighten a waist of a user.

Accordingly, a waistband device comprises a cushion, a first V-shaped connecting band disposed on a first lateral of the cushion, a second V-shaped connecting band disposed on a second lateral of the cushion, a first belt connected to the first V-shaped connecting band, a second belt connected to the second V-shaped connecting band, a first keeper disposed on the first belt, a first soft pad disposed on the first belt, a male fastener disposed on a distal end of the first belt, a first loop hole defined by the first belt, a second keeper disposed on the second belt, a second soft pad disposed on the second belt, a female fastener disposed on a distal end of the second belt, and a second loop hole defined by the second belt. The cushion surrounds a back of a waist of a user. The first loop hole and the second loop hole receive the knees of the user. The male fastener engages with the female fastener. The first keeper can adjust the size of the first loop hole. The second keeper can adjust the size of the second loop hole. When the user sits upright, the waistband device can help the user to straighten the waist.

DETAILED DESCRIPTION OF THE INVENTION

Figure 1:
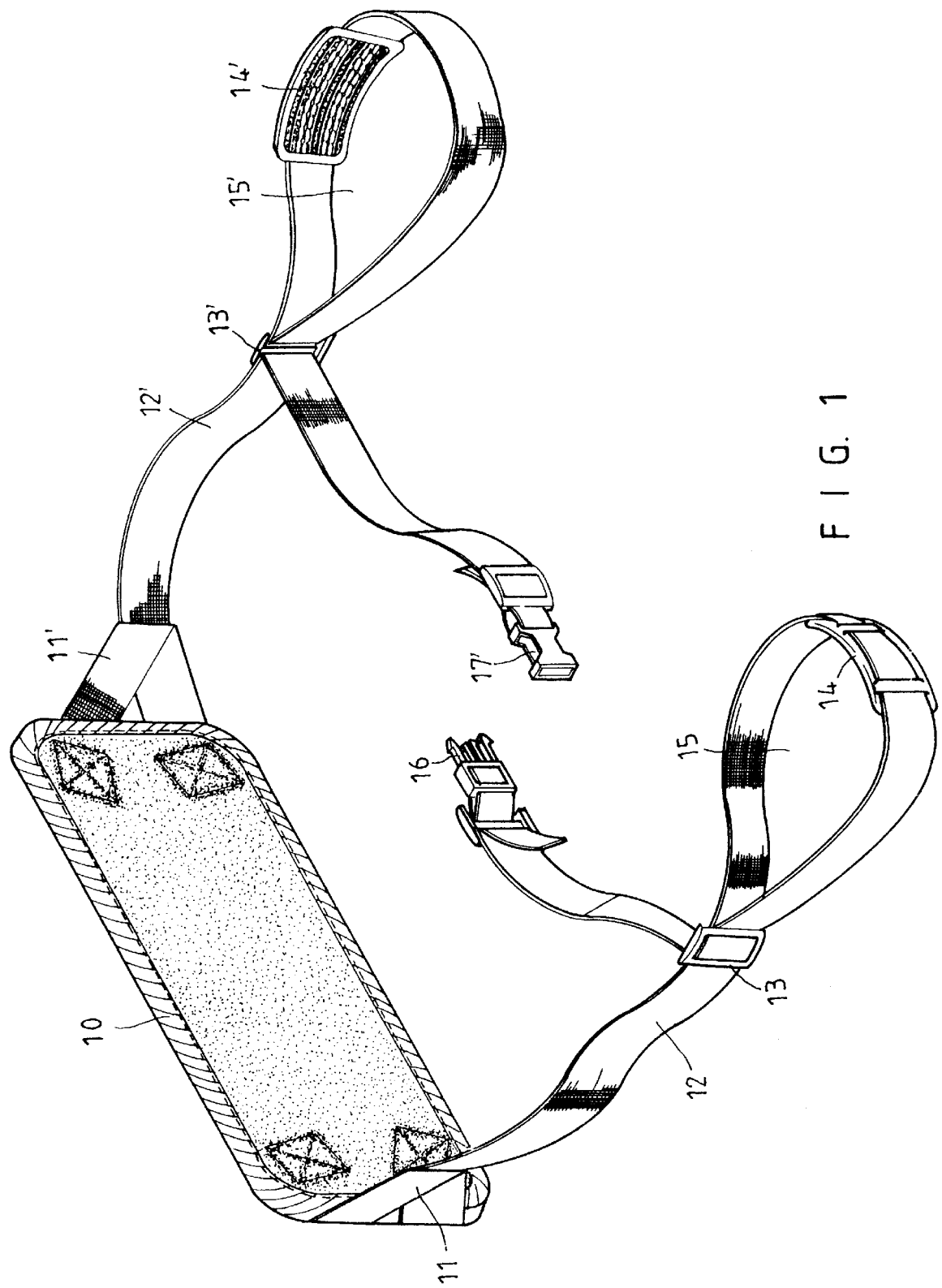
FIG. 1 is a perspective view of a waistband device of a preferred embodiment in accordance with the present invention.

Referring to FIG. 1, a waistband device comprises a rectangular cushion 10, a first V-shaped connecting band 11 disposed on a first lateral of the rectangular cushion 10, a second V-shaped connecting band 11' disposed on a second lateral of the rectangular cushion 10, a first belt 12 connected to the first V-shaped connecting band 11, a second belt 12' connected to the second V-shaped connecting band 11', a first keeper 13 disposed on the first belt 12, a first soft pad 14 disposed on the first belt 12, a male fastener 16 disposed on a distal end of the first belt 12, a first loop hole 15 defined by the first belt 12, a second keeper 13' disposed on the second belt 12', a second soft pad 14' disposed on the second belt 12', a female fastener 17' disposed on a distal end of the second belt 12', and a second loop hole 15' defined by the second belt 12'.

Figure 2:
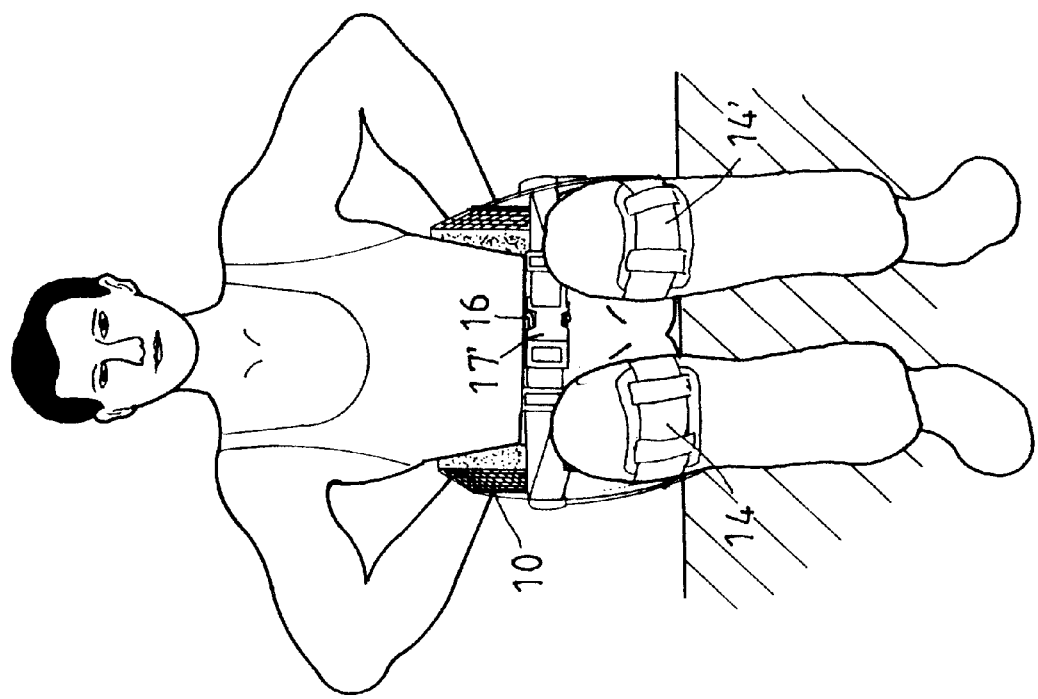
FIG. 2 is a perspective schematic view illustrating an application of a waistband device of a preferred embodiment in accordance with the present invention.
Figure 2A:
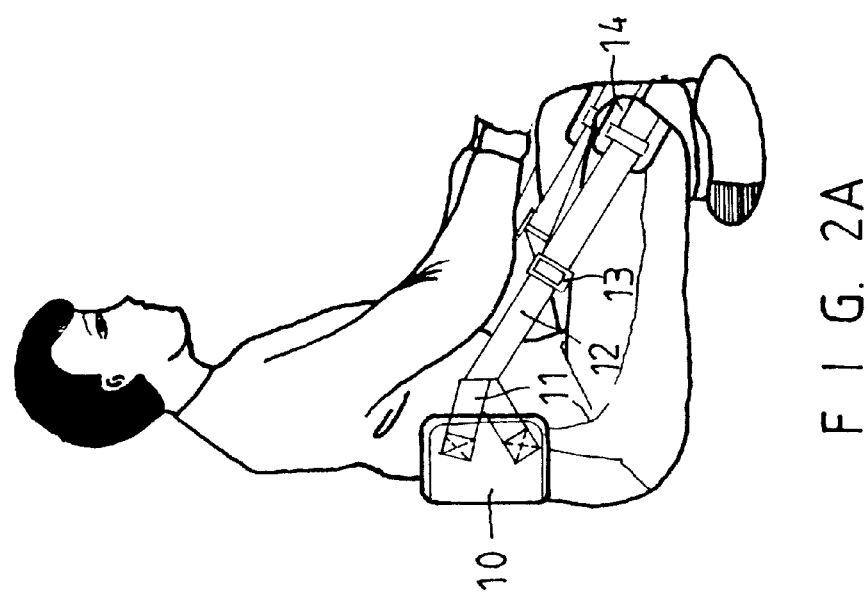
FIG. 2A is another perspective schematic view illustrating an application of a waistband device of a preferred embodiment in accordance with the present invention.
Figure 3:
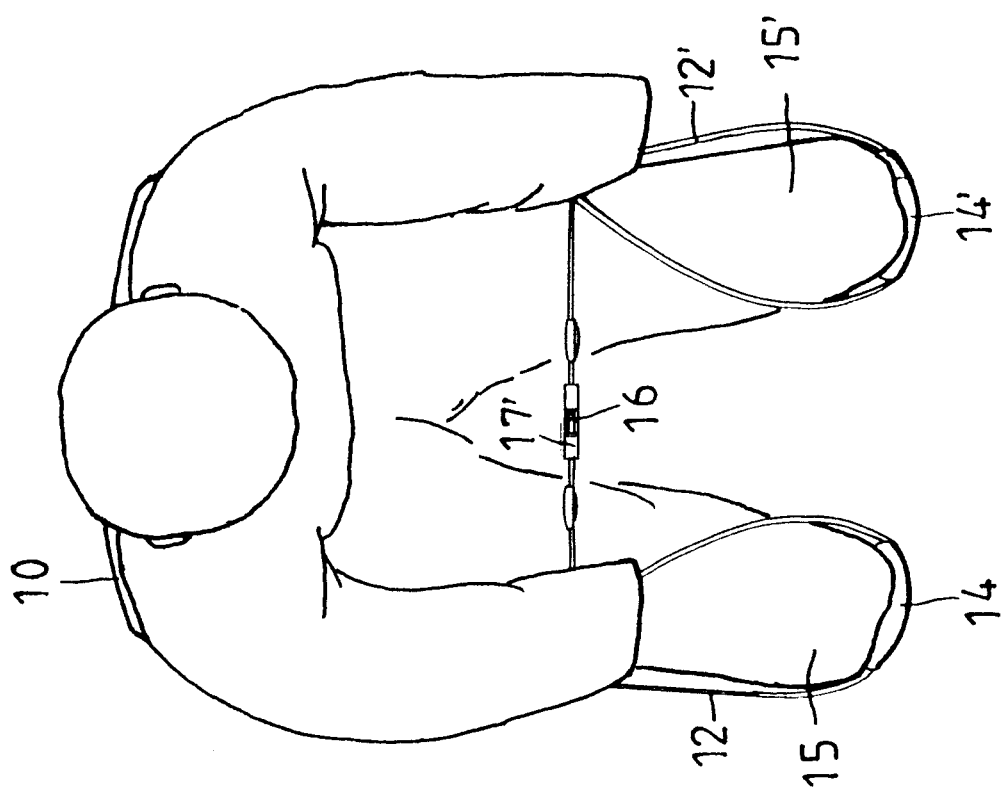
FIG. 3 is a top plan view of FIG. 2.

Referring to FIGS. 2, 2A and 3, the rectangular cushion 10 surrounds a back of a waist of a user. The first loop hole 15 and the second loop hole 15' receive the knees of the user. The male fastener 16 engages with the female fastener 17'. The first keeper 13 can adjust the size of the first loop hole 15. The second keeper 13' can adjust the size of the second loop hole 15'. When the user sits upright, the waistband device can help the user to straighten the waist.

The. knees helps the user to stretch the first V-shaped connecting band 11, the first belt 12, the second V-shaped connecting band 11', and the second belt 12'.

The present invention is not limited to the above embodiment but various modification thereof may be made. Furthermore, various changes in form and detail may be made without departing from the scope of the present invention.

I claim:

1. A waistband device comprising:
    a cushion,
    a first V-shaped connecting band disposed on a first lateral of the cushion,
    a second V-shaped connecting band disposed on a second lateral of the cushion,
    a first belt connected to the first V-shaped connecting band,
    a second belt connected to the second V-shaped connecting band,
    a first keeper disposed on the first belt,
    a first soft pad disposed on the first belt,
    a male fastener disposed on a distal end of the first belt,
    a first loop hole defined by the first belt,
    a second keeper disposed on the second belt,
    a second soft pad disposed on the second belt,
    a female fastener disposed on a distal end of the second belt, and
    a second loop hole defined by the second belt.

2. A waistband device as claimed in claim 1, wherein the cushion is in a rectangular shape.

* * * * *